US00PP10706P

United States Patent [19]

van Rijn

[11] Patent Number: Plant 10,706

[45] Date of Patent: Nov. 24, 1998

[54] ANTHURIUM PLANT NAMED 'LINDA'

[75] Inventor: Magdalena J. M. van Rijn, Schipluiden, Netherlands

[73] Assignee: Rijnplant, Schipluiden, Netherlands

[21] Appl. No.: 870,583

[22] Filed: Jun. 6, 1997

[51] Int. Cl.[6] ..... A01H 5/00

[52] U.S. Cl. ..... Plt./88.1

[58] Field of Search ..... Plt./88.1

*Primary Examiner*—Howard J. Locker
*Assistant Examiner*—Melissa L. Kimball
*Attorney, Agent, or Firm*—C. A. Whealy

[57] ABSTRACT

A distinct cultivar of Anthurium plant named 'Linda', characterized by its relatively large plant size; upright, outwardly arching and vigorous growth habit; freely branching plant habit; dark green leaves that are glossy and cordate in shape; numerous inflorescences that are positioned above the foliage on strong and erect peduncles; shiny dark red spathes; and good post-production longevity.

4 Drawing Sheets

The present invention relates to a new and distinct cultivar of Anthurium plant, botanically known as *Anthurium andreanum*, and hereinafter referred to by the cultivar name Linda.

The new cultivar is a product of a planned breeding program conducted by the inventor in Schipluiden, The Netherlands. The objective of the program is to create new Anthurium cultivars that have a freely branching growth habit, rapid growth rate, strong roots, attractive spathe color, numerous flowers and good post-production longevity. The new cultivar originated from a cross by the inventor between the proprietary *Anthurium andreanum* selection Nr. 6 as the female or seed parent and the proprietary *Anthurium andreanum* selection Nr. 3 as the male or pollen parent. The cultivar Linda was discovered and selected by the inventor as a plant within the progeny of the stated cross in a controlled environment in Schipluiden, The Netherlands.

Asexual propagation of the new cultivar at Schipluiden, The Netherlands, has shown that the unique features of this new Anthurium plant are stable and reproduced true to type in successive generations of asexual propagation.

The new Anthurium has not been observed under all possible environmental conditions. The phenotype may vary somewhat with variations in environment such as temperature and light intensity, without, however, any variance in genotype. The following observations, measurements and comparisons describe plants grown in Schipluiden, The Netherlands, in a glass greenhouse with an average day temperature of 25° C. and an average night temperature of 19° C.

The following traits have been repeatedly observed and are determined to be the unique characteristics of 'Linda'. These characteristics in combination distinguish 'Linda' as a new and distinct cultivar:

1. Relatively large plants that are upright, outwardly arching and vigorous in growth habit.
2. Freely branching plant habit.
3. Dark green leaves that are glossy and cordate in shape.
4. Numerous inflorescences that are positioned above the foliage on strong and erect peduncles.
5. Shiny dark red spathes.
6. Good post-production longevity.

The new Anthurium can be compared to its seed parent cultivar, the proprietary selection Nr. 6. In addition to spathe color, the new cultivar is different from plants of Nr. 6 in the following characteristics:

1. Plants of the cultivar Linda have smaller and more durable leaves than plants of the selection Nr. 6.
2. Plants of the cultivar Linda are more outwardly arching than plants of the selection Nr. 6 which are more upright.

3. Root development on plants of the cultivar Linda is more rapid than plants of the selection Nr. 6.
4. Plants of the cultivar Linda have darker green leaves than plants of the selection Nr. 6.
5. Plants of the cultivar Linda have smaller spathes and spadices than plants of the selection Nr. 6.

The new Anthurium can be compared to its pollen parent cultivar, the selection Nr. 3. Plants of the new cultivar Linda have larger leaves and larger and lighter red spathes than plants of the selection Nr. 3.

The new Anthurium can be compared to the nonpatented Anthurium cultivar Lady Jane. The new Anthurium differs from the cultivar Lady Jane in the following characteristics:

1. Plants of the cultivar Linda grow faster and flower earlier than plants of the cultivar Lady Jane.
2. Plants of the cultivar Linda have larger spathes and spadices than plants of the cultivar Lady Jane.
3. Plants of the cultivar Linda have darker red spathe color than plants of the cultivar Lady Jane.
4. Spathes of plants of the cultivar Linda are three times larger than spathes of plants of the cultivar Lady Jane.
5. Leaves of plants of the cultivar Linda have a cordate leaf base whereas leaves of plants of the cultivar Lady Jane have an acute leaf base.

The accompanying colored photographs illustrate the overall appearance of the new cultivar, showing the colors as true as it is reasonably possible to obtain in colored reproductions of this type.

The first photograph comprises a top perspective view of a typical potted plant of 'Linda'.

The second photograph comprises a close-up view of a typical spathe and spadix of 'Linda'.

The third photograph comprises a close-up view of a typical young leaf of 'Linda'.

The fourth photograph comprises a close-up view of a typical mature leaf of 'Linda'. Leaf and flower colors in the photographs may appear different from the actual colors due to light reflectance.

In the following description, color references are made to The Royal Horticultural Society Colour Chart except where general terms of ordinary dictionary significance are used.

Botanical classification: *Anthurium andreanum* cultivar Linda.

Parentage:

*Seed or female parent.*—Inventor's proprietary *Anthurium andreanum* selection Nr. 6.

*Pollen or male parent.*—Inventor's proprietary *Anthurium andreanum* selection Nr. 3.

Propagation:

*Method.*—By tissue culture.

*Time to initiate roots.*—70 and 84 days at 24° and 21° C. soil temperatures, respectively.

Plant description:

*Plant shape.*—Upright, inverted triangle, symmetrical.

*Growth habit.*—Erect when young, becoming outwardly arching as leaves develop. Freely branching. Appropriate for 17 to 70-cm containers.

*Rooting habit.*—Freely branching, numerous fleshy roots.

*Plant height.*—70 to 90 cm from soil level to top of leaf plane.

*Plant vigor.*—High.

*Growth rate.*—Moderate.

*Crop time.*—About 16 to 17 months are usually required from planting of a young plant to a finished plant with a height of 65 to 70 cm.

*Foliage description.*—Quantity of leaves per finished plant: About 60. Leaf shape: Cordate. Leaf apex: Apiculate. Leaf base: Cordate, not overlapping lobes. Leaf margin: Entire. Leaf texture: Leathery, smooth, glabrous, glossy. Leaf size: Length: 22 to 32 cm. Width: 17 to 20 cm. Leaf color: Young, adaxial surface: Brownish red to dark green. Young, abaxial surface: Brownish red to dark green. Mature, adaxial surface: Between 139A and 147A. Mature, abaxial surface: Darker than 144A. Venation, adaxial surface: Same as surrounding tissue. Venation, abaxial surface: Darker green than surrounding tissue. Petiole length, primary shoot: 40 to 70 cm. Petiole color: 144A.

Flower Description:

*Flower arrangement.*—Spathe with spadix held above the foliage. Flowers arise from leaf axils.

*Flower longevity.*—Spathe/spadix last about 6 weeks under winter conditions and up to 3 months under summer conditions, persistent.

*Quantity of flowers per spadix.*—150 to 200.

*Flower shape.*—Rounded.

*Flower diameter.*—About 1 mm.

*Spathe.*—Appearance. Shiny. Shape: Deltoid. Apex: Apiculate/cuspidate. Base: Cordate, not overlapping lobes. Margin: Entire. Texture: Slightly blistered. Size: Length: 10 to 13 cm. Width: 8 to 10 cm. Color: When opening: 45A. Open flower, adaxial surface: 45A. Open flower, abaxial surface: 51A/51B. After senescence: Darker than 46A.

*Spadix.*—Cross section: Rounded. Longitudinal axis: Very weakly recurved. Size: Length: 7 to 9 cm. Diameter: About 1 cm. Color: Base: Cream white. Mature: Close to 22C. Apex: 40C/40D. After senescence: 151C/144C.

*Peduncle.*—Aspect: Strong and erect. Length: 60 to 90 cm. Color: 144A at base, darker green with red overtones at apex.

*Reproductive organs.*—Androecium: Pollen color: Cream white, 158D. Gynoecium: Stigma shape: Ovoid. Ovary: Protogyneous.

Disease resistance: Not susceptible to root pathogens.

Seed development: Seed development is rarely observed.

It is claimed:

1. A new and distinct cultivar of Anthurium plant named 'Linda', as illustrated and described.

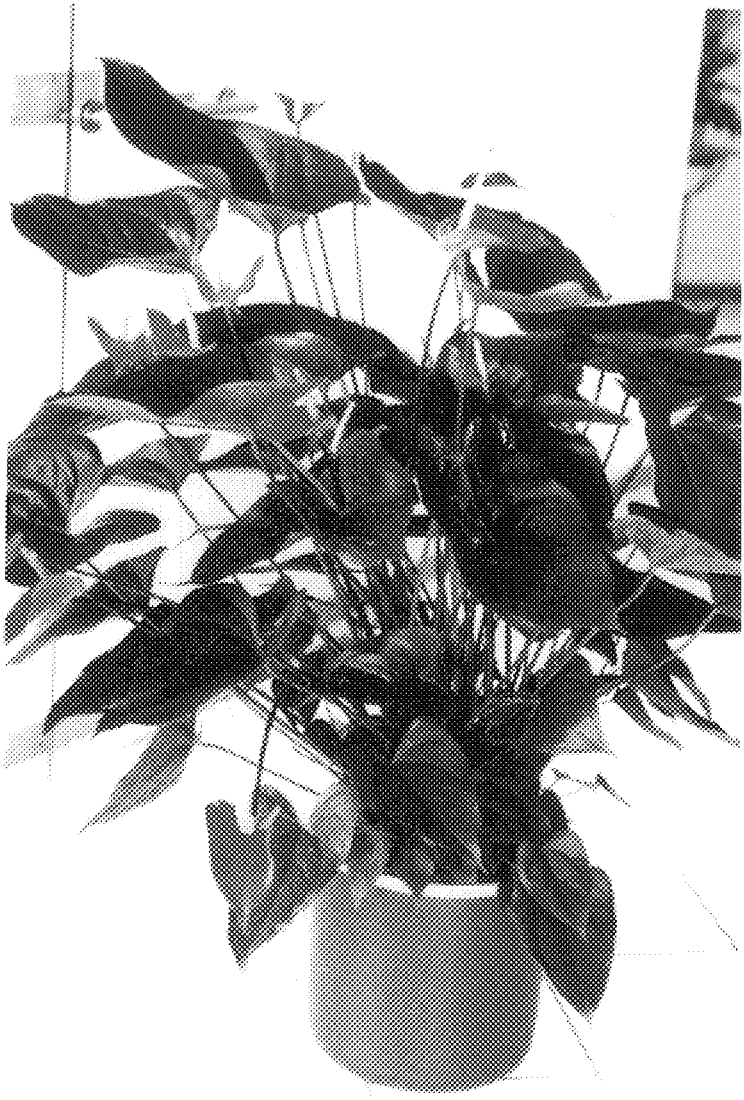

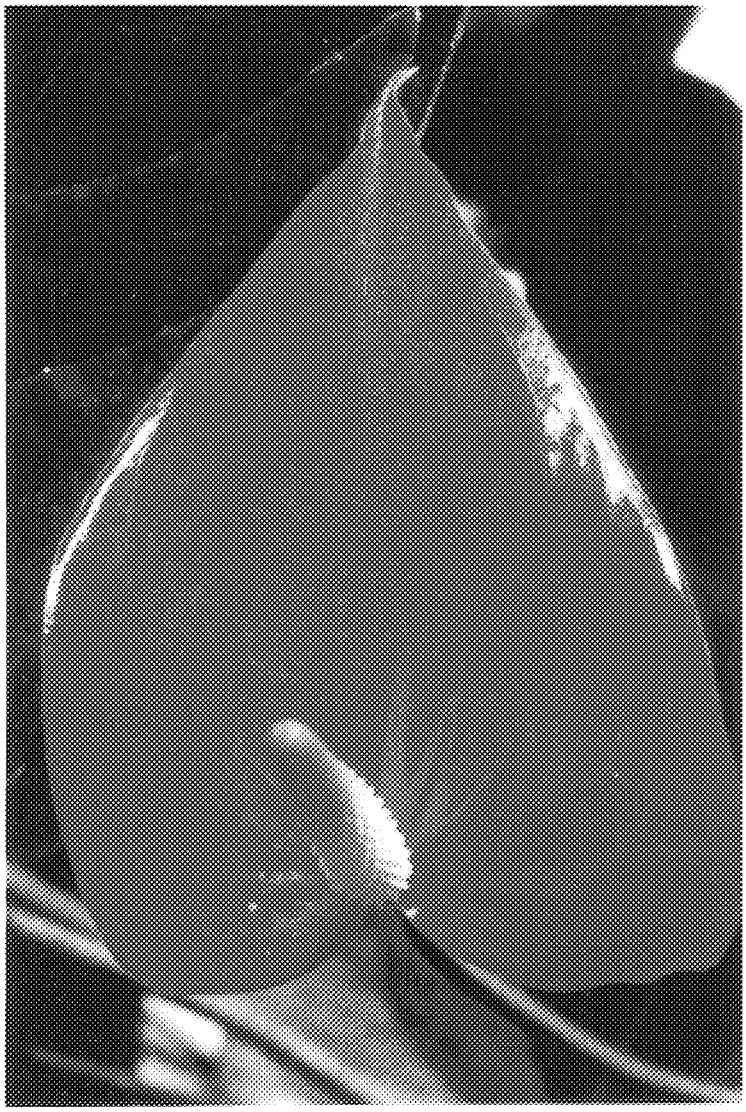

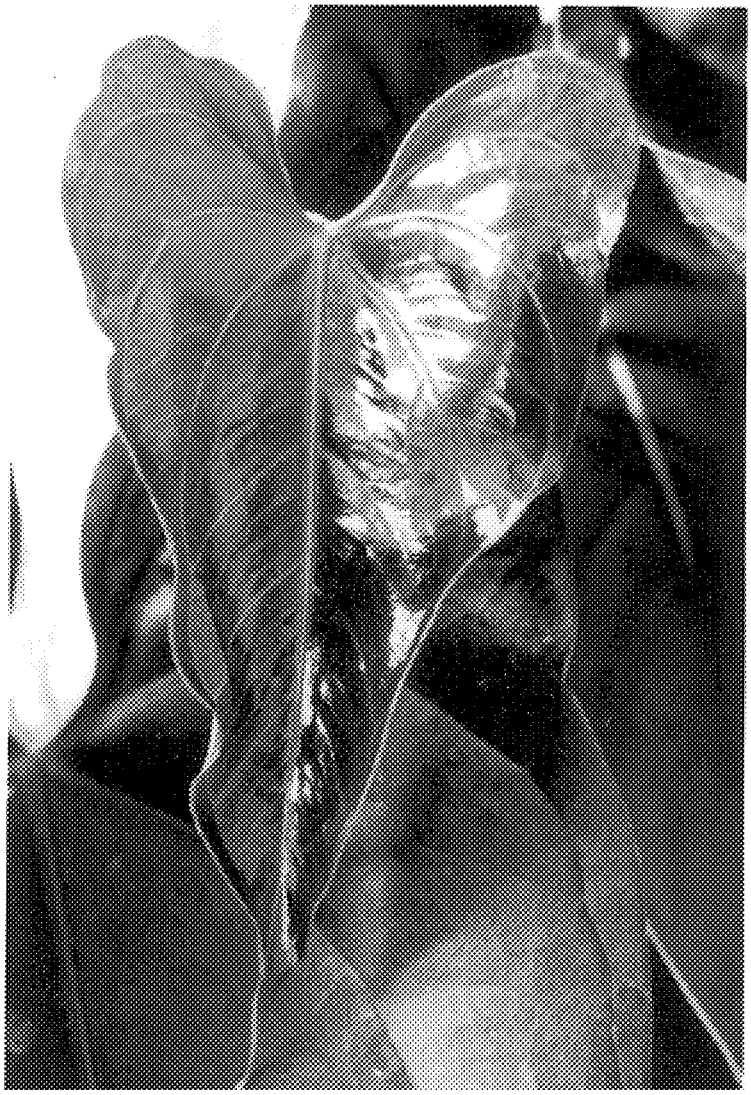

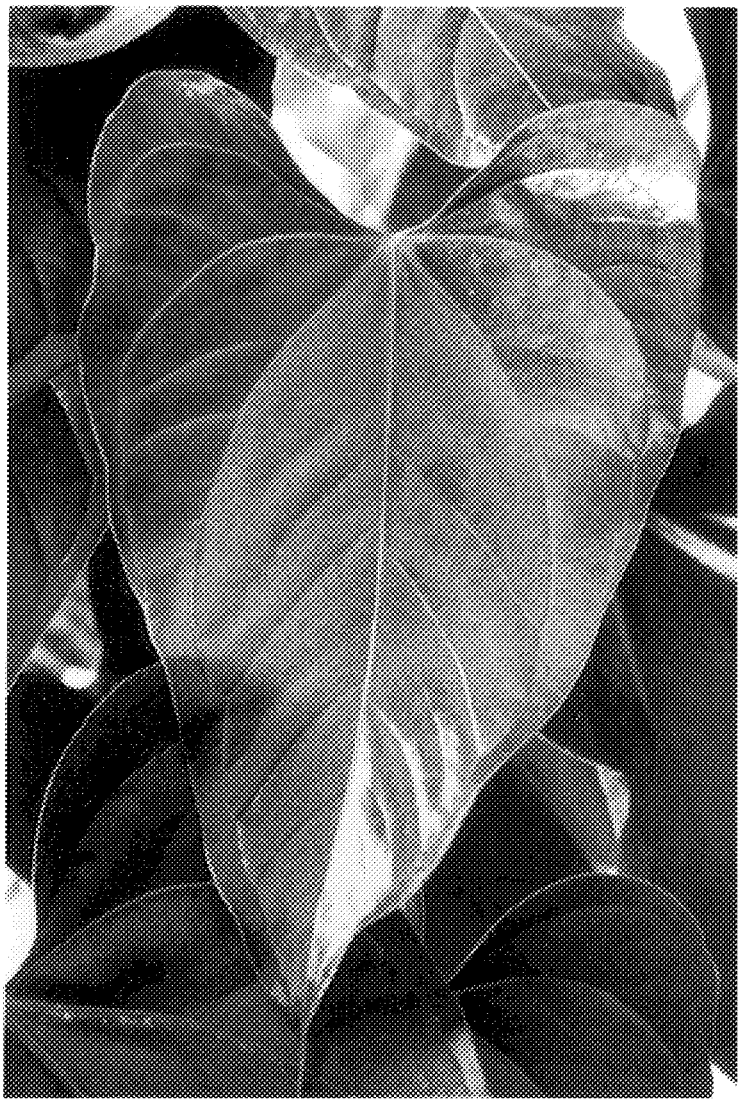

* * * * *